United States Patent [19]
Michel et al.

[11] Patent Number: 5,385,927
[45] Date of Patent: Jan. 31, 1995

[54] HYDROXY-3-[1-(1H-IMIDAZOL-4-YL)AL-KYL]-BENZENECARBOXIMIDAMIDES AND THEIR USE IN TREATING GLAUCOMA

[75] Inventors: Philippe Michel, Beersel; Eric Cossement, Bruxelles; Jean Gobert, Bruxelles; Ernst Wülfert, Bruxelles, all of Belgium

[73] Assignee: U C B, S.A., Brussels, Belgium

[21] Appl. No.: 248,205

[22] Filed: May 24, 1994

[30] Foreign Application Priority Data

May 27, 1993 [DE] Germany .............. 9310965

[51] Int. Cl.$^6$ ............. A61K 31/535; C07D 413/10; C07D 233/64
[52] U.S. Cl. ................. 514/397; 514/400; 548/314.4; 548/346.1
[58] Field of Search ......... 548/314.4, 346.1; 514/397, 400

[56] References Cited

U.S. PATENT DOCUMENTS 4,814,343  3/1989  Cossement ............ 514/397
4,923,865  5/1990  Cossement ............ 514/235.8

FOREIGN PATENT DOCUMENTS

WO92/09583  6/1992  WIPO .

OTHER PUBLICATIONS

Huber et al., Journal of Medicinal Chemistry, vol. 34, No. 11, 1991, pp. 3197-3204.

Noyer et al., Chemical Abstracts, vol. 120, No. 23, 1994, Abstract No. 290600f.

*Primary Examiner*—Mary C. Lee
*Assistant Examiner*—Jacqueline Haley
*Attorney, Agent, or Firm*—Wenderoth, Lind & Ponack

[57] ABSTRACT

New 2-hydroxyl-3-[1-(1H-imidazol-4-yl)alkyl]-benzenecarboximidamides as well as their salts, having the formula

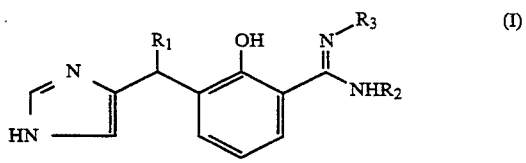

(I)

wherein $R_1$ is hydrogen or an alkyl radical having 1 to 4 carbon atoms, $R_2$ is hydrogen a hydroxyl group, an amino group or an alkyl radical having 1 to 4 carbon atoms, $R_3$ is hydrogen, or $R_2$ and $R_3$ together are —CH$_2$—CH$_2$—;

processes for the preparation thereof, and ophthalmic compositions comprising the same are also described. These compounds are capable of lowering intraocular pressure and can be used in the prevention and treatment of glaucoma.

12 Claims, No Drawings

HYDROXY-3-[1-(1H-IMIDAZOL-4-YL)ALKYL]-BENZENECARBOXIMIDAMIDES AND THEIR USE IN TREATING GLAUCOMA

The present invention relates to new substituted 2-hydroxy-3-[1-[1H-imidazol-4-yl)alkyl]-benzenecarboximidamides, to the non-toxic ephthalmologically acceptable acid addition salts thereof, as well as to processes for the preparation and use thereof in the prevention and treatment of glaucoma.

It also relates to ophthalmic compositions containing the said compounds.

U.S. Pat. No. 4,814,343 (assigned to the assignee of the present invention) describes substituted 1H-imidazoles, the most representative of which are 2-hydroxy-3-[1-(1H-imidazol-4-yl)alkyl]-benzenemethanols. These 1H-imidazoles have cardiac, cerebral and tissular anti-ischemic properties.

U.S. Pat. No. 4,923,865 (also assigned to the assignee of the present invention) describes substituted [1-(1H-imidazol-4-yl)alkyl]-benzamides which, not only possess cardiac, cerebral and tissular anti-ischemic properties, but also possess $\alpha_2$-adrenergic receptor agonist properties. The latter properties confer to these compounds a beneficial therapeutic usefulness in the treatment of disorders giving rise to, or resulting from an abnormal increase of the catecholamine levels, such as, for example, cardiac congestion, Raynaud's disease or spasms of the coronary arteries. For the same reason, these compounds can also be used in the treatment of disorders associated with gastric and intestinal hypersecretions, as well as in the treatment of the drug withdrawal syndrome of the toxicomaniacs. In addition, these compounds possess a certain diuretic activity.

Continuing research work in this field, we have now synthesized new substituted 2-hydroxy-3-[1-(1H-imidazol-4-yl)alkyl]-benzenecarboximidamides which are strong $\alpha_2$-adrenergic receptor agonists, while exhibiting little or even no systemic side-effects of central or peripheral origin. For this reason, these compounds can be advantageously used to reduce intraocular pressure, more particularly in the prevention and the treatment of glaucoma.

Glaucoma is a disease of the eye characterized by an increase in intraocular pressure, resulting in hardening of the eyeball, atrophy of the optic nerve with characteristic excavation of the papilla, narrowing of the field of vision and a more or less important decrease in visual acuity. The terminal stage of glaucoma (or absolute glaucoma) is accompanied by total blindness of the patient.

Emergency treatment of glaucoma usually consists in the topical application of cholinergic agents such as pilocarpine, of $\alpha$- or $\beta$-adrenergic agonists or antagonists such as clonidine, timolol or epinephrine, or of carbonic anhydrase inhibitors by systemic administration. Finally, in the last resort, it is sometimes necessary to perform a surgical operation.

However, the various conventional treatments of glaucoma available at present are often accompanied by side-effects, the nature and gravity of which is very variable.

Thus, instillation of a cholinergic agent, such as pilocarpine, into the eye can give rise in some patients to nausea, diarrhea, muscular spasms, sweating, lacrimation, salivation, and the like. At the very eye level, contraction of the pupil (myosis) and of the ciliary muscle, as well as dilation of the blood vessels of the iris and conjunctiva can be observed. Visual complications very often follow, such as the spasm of accommodation, myopia or a decrease in visual acuity.

The treatment with a sympathomimetic agent such as dipivalylepinephrine is known to produce frequently sensations of burning or irritation. Furthermore, an important side-effect of these agents is the appearance of cardiac disturbances including palpitations, tachycardia, arrythmia, and the like.

Clonidine, which is known as an $\alpha_2$-adrenergic receptor agonist, can bring about mydriasis, as well as an initial phase of ocular hypertension (biphasic effect). Furthermore, in spite of the topical application of the product to the eye, important systemic effects, such as bradycardia and hypotension, have been observed.

The use of $\beta$-blocking medicaments also can cause important systemic effects after topical administration to the eye, due to the absence of a "first pass effect". Timolol, for example, causes bradycardia or hypotension. These systemic secondary reactions to $\beta$-blocking medicaments can reach such a severe level that the treatment has to be discontinued. Cases of suicidal depression, hallucinations, nightmares or psychoses requiring hospitalization have been reported in connection with these medicaments. Furthermore, these compounds have to be administered with extreme precautions to patients subject to cardiac or pulmonary functional disorders. In such patients, amongst others, cases of arrythmia, cardiac arrest, asthma, dyspnea and bronchospasms have been reported.

The treatment with a sympatholytic agent, such as guanethidine, causes hyperemia of the conjunctiva and some irritation, not to mention the fact that these agents only have a low tendency to reduce intraocular pressure.

Finally, in the treatment of glaucoma with carbonic anhydrase inhibitors, such as acetazolamide or methazolamide, serious systemic side-effects, such as depression of the central nervous system, weight loss and, mainly, bone marrow hypofunction, have been reported.

Thus, it is clearly apparent that the use of conventional hypotensive agents for the treatment of glaucoma is accompanied by considerable risks. Known medications are not particularly well suited for topical treatment and the systemic side-effects of these medicaments make them delicate to use because these effects are far from being negligeable and because they can have, in some cases, severe consequences.

Therefore, there is a real need to find new drugs capable of effectively lowering intraocular pressure and which, at the same time, do not have the above-mentioned systemic side-effects, particularly when administered to so-called "at-risk" patients, such as cardiac and asthmatic patients.

We have now found that the new substituted 2-hydroxy-3-[1-(1H-imidazol-4-yl)alkyl]-benzenecarboximidamides perfectly fulfil this long wanted need. Indeed, these compounds are potent presynaptic $\alpha_2$-adrenergic receptors agonists. Moreover, these compounds do not exhibit systemic side-effects of central or peripheral origin, since at a dosage at which these compounds are effective to lower intraocular pressure, neither hypotension, nor bradycardia, nor mydriasis have been observed. Furthermore, these compounds do not induce hypohemia of the treated eye, nor has any contralateral side-effect been observed in the untreated eye after topical treatment of its pair, thus showing very well the absence of relay, either through the blood circulation or through the neuronal system. Since the risks associated with the therapeutic agents conventionally used for the treatment of glaucoma, are practically inexistent with the compounds of the present invention, the substituted 2-hydroxy-3-[1-(1H-imidazol-4-yl)alkyl]-benzenecarboximidamides according to the present invention are particularly well suited to the treatment of intraocular hypertension, and particularly of glaucoma.

More particularly, the present invention relates to new substituted 2-hydroxy-3-[1-(1H-imidazol-4-yl)alkyl]-benzenecarboximidamides having the general formula:

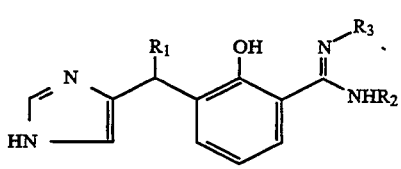

wherein $R_1$ represents a hydrogen atom or an alkyl radical having 1 to 4 carbon atoms, $R_2$ represents a hydrogen atom, a hydroxyl group, an amino group or an alkyl radical having 1 to 4 carbon atoms, $R_3$ represents a hydrogen atom, or $R_2$ and $R_3$ taken together represent a —CH$_2$–CH$_2$— group, and to the non-toxic ophthalmologically acceptable acid addition salts thereof.

When the molecule contains an asymmetric carbon atom, the compounds of formula I may be either in the form of a racemic mixture or in the form of one of the enantiomers. These various forms also fall within the scope of the present invention.

The present invention also relates to the non-toxic ophthalmologically acceptable acid addition salts of the substituted 2-hydroxy-3-[1-(1H-imidazol-4-yl)alkyl]-benzenecarboximidamides of formula I. Any acid addition salt may be used, provided that it is of low toxicity and is non-irritating to the eye. Examples of ophthalmologically acceptable acids are set forth on page 2 of Journal of Pharm. Sciences 66(1), (1977) and include among others phosphoric acid, maleic acid, boric acid, carbonic acid and the like.

Preferred compounds according to the present invention include:

2-hydroxy-3-(1H-imidazol-4-ylmethyl)-benzenecarboximidamide;

N,2-dihydroxy-3-(1H-imidazol-4-ylmethyl)-benzenecarboximidamide;

2-hydroxy-3-(1H-imidazol-4-ylmethyl)-N-methyl-benzenecarboximidamide;

2-hydroxy-3-(1H-imidazol-4-ylmethyl)-N-(1-methylethyl)-benzenecarboximidamide;

2-hydroxy-3-(1H-imidazol-4-ylmethyl)-benzenecarboximidic acid hydrazide;

(+)-2-hydroxy-3-[1-(1H-imidazol-4-yl)ethyl]-benzenecarboximidamide; and (−)-2-hydroxy-3-[1-(1H-imidazol-4-yl)ethyl]-benzenecarboximidamide.

The substituted 2-hydroxy-3-[1-(1H-imidazol-4-yl)alkyl]-benzenecarboximidamides of formula I can be prepared by a general process which comprises the following steps:

(1) a 2-hydroxy-3-[1-(1H-imidazol-4-yl)alkyl]-benzonitrile of the formula II is reacted with an alkanol having 1 to 4 carbon atoms in the presence of gaseous hydrochloric acid according to the equation:

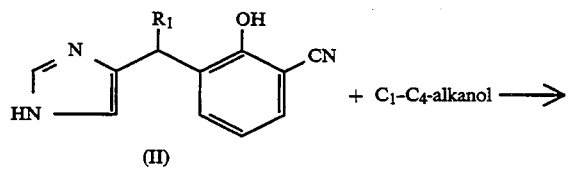

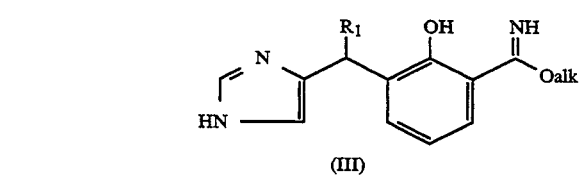

This reaction is generally carried out at a temperature between −45° C. and +15° C.

(2) next, the resulting alkyl 2-hydroxy-3-[1-(1H-imidazol-4-yl)alkyl]-benzenecarboximidate of the formula III is reacted with one of the enantiomers of α-methylbenzylamine, according to the equation:

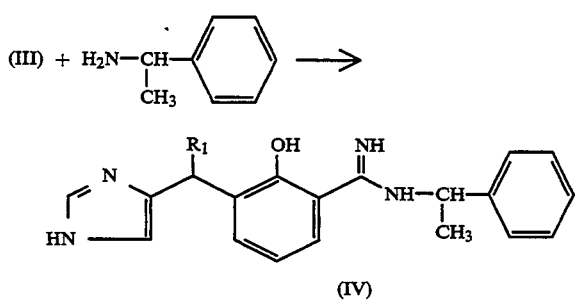

(3) finally, the 2-hydroxy-3-[1-(1H-imidazol-4-yl)alkyl]-N-α-methylbenzyl-benzenecarboximidamide of the formula IV obtained in the preceding step is reacted with a nitrogen compound of the formula R$_2$NH$_2$ (V), in which R$_2$ represents a hydrogen atom, a hydroxyl group, an amino group or an alkyl radical having 1 to 4 carbon atoms when R$_3$ is a hydrogen atom, or with ethylenediamine (VI) when R$_2$ and R$_3$, taken together, represent the —CH$_2$–CH$_2$— group, according to the equation:

In all the above formulae, $R_1$ has the meaning given above and alk represents an alkyl radical having 1 to 4 carbon atoms.

It is obvious that, in order to obtain the compounds of general formula I in the form of an optical isomer, the N-α-methylbenzyl diastereoisomers of the formula IV in which $R_1$ is an alkyl radical having 1 to 4 carbon atoms, are separated prior to the aminolysis reaction of step (3).

This general process, thus, is eminently suitable to prepare all the compounds of general formula I, either in the form of a racemic mixture or in the form of an optical isomer when R₁ represents an alkyl radical having 1 to 4 carbon atoms, or also in an optically inactive form when the molecule does not contain an asymmetric carbon atom (R₁=hydrogen).

According to a particular embodiment, directed to the preparation of the 2-hydroxy-3-[1-(1H-imidazol-4-yl)alkyl]-benzenecarboximidamides of general formula I, an alkyl 2-hydroxy-3-[1(1H-imidazol-4-yl)alkyl]benzenecarboximidate of the formula III is first synthesized by carrying out only step (1) of the above described process, and the resulting alkyl benzenecarboximidate of the formula III is then reacted with a nitrogen compound of the formula R₂-NH₂ (V), in which R₂ represents a hydrogen atom, a hydroxyl group, an amino group or an alkyl radical having 1 to 4 carbon atoms when R₃ is a hydrogen atom, or with ethylenediamine (VI) when R₂ and R₃, taken together, represent the —CH₂-CH₂— group.

As an alternative process, specific to the preparation of the 2-hydroxy-3-[1-(1H-imidazol-4-yl)alkyl]-benzenecarboximidamides of general formula I, in which R₂ represents a hydroxyl group and R₃ represents a hydrogen atom, hydroxylamine is reacted with a 2-hydroxy-3-[1-(1H-imidazol-4-yl)alkyl]benzonitrile of the formula II, in which R₁ has the meaning given above.

In the particular case of the preparation of the 2-hydroxy-3-[1(1H-imidazol-4-yl)alkyl]-benzenecarboximidamides of general formula I, in which R₁ represents an alkyl radical having 1 to 4 carbon atoms, and R₂ and R₃ represent both a hydrogen atom, in the form of their optical isomers, a 2-hydroxy-3-[1-(1H-imidazol-4-yl)alkyl]-N-α-methylbenzyl-benzenecarboximidamide of the formula IV is first synthesized by carrying out only steps (1) and (2) of the above described process, the resulting N-α-methylbenzyl diastereoisomers of the formula IV are separated, and thereafter the α-methylbenzyl group of each diastereoisomer, thus separated, is removed by hydrolysis with concentrated hydrochloric acid at a temperature of from 80° C. to 110° C.

The non-toxic ophthalmologically acceptable acid addition salts can be prepared from the 2-hydroxy-3-[1-(1H-imidazol-4-yl)alkyl]-benzenecarboximidamides of the formula I by methods which are known per se.

The 2-hydroxy-3-[1-(1H-imidazol-4-yl)alkyl]-benzonitriles of the formula II used as starting materials, can be prepared according to the process described in U.S. Pat. No. 4,923,863.

As indicated above, the substituted 2-hydroxy-3-[1-(1H-imidazol-4-yl)alkyl]-benzenecarboximidamides of the formula I as well as their non-toxic ophthalmologically acceptable acid addition salts possess presynaptic α₂-adrenergic receptors agonist properties, are capable of lowering intraocular tension, and are free from significant side-effects.

The pharmacological tests described hereinafter demonstrate these various advantageous properties.

The following compounds have been subjected to pharmacological tests:

2-hydroxy-3-(1H-imidazol-4-ylmethyl)-benzenecarboximidamide (compound A, prepared in example 2.1);
2-hydroxy-3-(1H-imidazol-4-ylmethyl)-N-methyl-benzenecarboximidamide (compound B, prepared in example 2.2);
N,2-dihydroxy-3-(1H-imidazol-4-ylmethyl)-benzenecarboximidamide (compound C, prepared in example 3);
(+)-2-hydroxy-3-[1-(1H-imidazol-4-yl)ethyl]-benzenecarboximidamide (compound D, prepared in example 4);
(−)-2-hydroxy-3-[1-(1H-imidazol-4-yl)ethyl]-benzenecarboximidamide (compound E, prepared in example 4);
2-hydroxy-3-(1H-imidazol-4-ylmethyl)-N-(1-methylethyl)-benzenecarboximidamide (compound F, prepared in example 5.2); and
2-hydroxy-3-(1H-imidazol-4-ylmethyl)-benzenecarboximidic acid hydrazide (compound G prepared in example 2.6).

The results have been compared to those obtained with clonidine, an α₂-adrenergic receptor agonist which, like some of its derivatives, is used in the treatment of glaucoma.

1. Presynaptic α₂-adrenergic receptor agonist properties.

Stimulation of the guinea-pig ileum.

The presynaptic α₂-adrenergic agonist properties of the compounds according to the invention are demonstrated by measuring the inhibition of the contraction of the isolated guinea-pig ileum induced by electrical stimulation.

Longitudinal muscle fragments attached to an isometric force indicator are immersed in Tyrode's solution and are stretched with a force of 1 g (G. M. DREW, Brit. J. Pharmacol. 64, (1978), 293–300; M. ANDREJAK et al., Naunyn-Schmiedeberg's Arch. Pharmacol. 314, (1980), 83–87).

Electrical stimulation of the parasympathetic nerves associated with the ileum fragments causes a contraction of the muscle. This contraction is reduced in the presence of a presynaptic α₂-agonist and the magnitude by which the contraction is reduced depends on the concentration of the agonist used. This effect is antagonized by the simultaneous presence of an α₂-antagonist such as α-yohimbine.

The compounds to be studied have been tested at increasing concentrations ranging from $10^{-10}$ to $10^{-3}$ mole/l. The concentration (IC₅₀ in mole/l) that reduces by 50% the intensity of the muscle contraction is determined.

Table I gives the IC₅₀ concentrations (in mole/l) obtained for the compounds of the invention (except for compound 6, for which compound the IC₃₀ concentration is given). These results show that these compounds are highly active at very low concentration.

TABLE I

| Inhibition of the contraction of the guinea-pig ileum | |
|---|---|
| Compound | IC₅₀ (in mole/l) |
| A | $6.2 \times 10^{-8}$ |
| B | $2.5 \times 10^{-6}$ |
| C | $1.4 \times 10^{-7}$ |
| D | $3.9 \times 10^{-9}$ |
| E | $2.0 \times 10^{-7}$ |
| F | $6.4 \times 10^{-6}$ |
| G | $2.5 \times 10^{-6}$ (IC₃₀) |
| clonidine | $1.7 \times 10^{-8}$ |

2. Intraocular hypotensive activity.

The intraocular pressure lowering effect of the compounds is demonstrated in awake normotensive rabbits (New Zealand White), by measuring the intraocular pressure variation after a unilateral application of the compounds into the left eye of the animals. All the doses tested are administered to three rabbits (weight 2-2.5 kg) of both sexes according to a "cross-over" experimental protocol in which each animal is also used in the control group. The compounds to be studied, as well as clonidine, are administered as a solution (which has been left standing at ambient temperature for 30 minutes prior to administration), in 30 microliters of sterile distilled water (collyrium) at concentrations ranging from 0 (reference) to 0.5% (in weight per volume). The intraocular pressure is measured tonometrically with a BIORAD pneumatonograph (DIGILAB MODULAR ONE) after local anesthesia using 2 drops of a 0.4% (in weight per volume) solution of oxybuprocaine hydrochloride.

Table II below shows the variations in pressure observed by instillation of the compounds according to the invention as well as of clonidine. In this Table, the 1st column indicates the compound tested, the 2nd column indicates the concentration of the compound, in percent (in weight per volume), the 3rd, 4th, 5th, 6th and 7th columns indicate the variation in intraocular pressure ($\Delta P$) expressed in percent, with respect to an animal treated with a collyrium containing no compound to be tested, measured after 30 minutes, 1, 2, 3 or 6 hours respectively.

TABLE II

| | | Fall in intraocular pressure | | | | |
|---|---|---|---|---|---|---|
| Compound | Conc. (%) | $\Delta P$ [30 min] (%) | $\Delta P$ [1 h] (%) | $\Delta P$ [2 h] (%) | $\Delta P$ [3 h] (%) | $\Delta P$ [6 h] (%) |
| A | 0.05 | −5.9 | | −18.6 | | −1.1 |
| | 0.1 | −9.2 | | −21.2 | | −16.1 |
| B | 0.5 | −5.5 | −10.8 | −13.3 | −12.8 | −7.6 |
| D | 0.01 | −14.1 | | −17.7 | | −15.1 |
| E | 0.5 | −11.6 | −12.6 | | | −6.6 |
| clonidine | 0.01 | +8.0 | | −8.8 | | −9.2 |
| | 0.1 | +23.4 | | +36.2 | +11.4 | |
| | 0.5 | +31.4 | | +39.4 | +8.6 | |

This Table shows that the compounds according to the invention have a good intraocular hypotensive activity, as opposed to clonidine which initially induces hypertension of the treated eye, which effect increases with the concentration of the product. This biphasic effect of clonidine is not observed with the compounds according to the invention.

Furthermore, the compounds according to the invention do not induce a concomitant reduction of the intraocular pressure of the contralateral eye of the treated animals. With clonidine, however, the following variations in intraocular pressure in the contralateral eye are measured:

at a concentration of 0.01%, $\Delta P = -9.5\%$ after 2 hours and $-9.2\%$ after 6 hours;

at a concentration of 0.1%, $\Delta P = -10.2\%$ after 2 hours and $+2.6\%$ after 6 hours;

at a concentration of 0.5%, $\Delta P = -26.3\%$ after 2 hours and $+15\%$ after 6 hours.

This demonstrates the absence of relay of the compounds according to the invention, either through the blood circulation or through the neuronal system. Furthermore, these results show how difficult it is to obtain a reduction of the intraocular pressure using clonidine, because of its biphasic effect.

3. Effects on the pupil diameter of the treated eye and of the contralateral eye.

The effect of the compounds according to the invention on the diameter of the pupil is demonstrated in awake normotensive rabbits (New Zealand White) of both sexes (weight 2-2.5 kg), by measuring the variation of the diameter of the pupils of both eyes after topical application of the compounds into the left eye of the animals. The compounds to be studied, as well as clonidine, are administered as a solution (which had been left standing at ambient temperature for 30 minutes prior to administration), in 30 microliters of sterile distilled water (collyrium) at concentrations ranging from 0 (reference) to 0.5% (in weight per volume). The pupil diameters are measured visually at the point of maximal vertical diameter, using a millimetric metal standard.

The compounds according to the invention do not induce or induce only a slight significant change in the pupil diameters at doses at which they lower ocular pressure (Table II), regardless of which eye is measured (treated or contralateral). As a matter of fact, the maximum differences between the pupil diameters measured before instillation of the compound to be tested and the pupil diameters measured at observation times of between 30 minutes and 6 hours after instillation of the compound to be tested ranges from $-4.2\%$ to $+4.7\%$.

Table III shows the results observed under the same conditions with clonidine. In this Table, the 1st column gives the concentration of clonidine, in percent (weight/volume);

the 2nd column gives the maximum difference observed between the pupil diameter of the treated eye (ipsilateral) measured before instillation of clonidine and the pupil diameter of the same eye, measured at observation times of between 30 minutes and 6 hours after instillation;

the 3rd column gives the maximum difference measured under the same conditions on the diameter of the pupil of the contralateral eye.

TABLE III

| Effect of clonidine on the pupil diameter | | |
|---|---|---|
| Clonidine concentration (%) | Maximum difference (ipsilateral eye) (%) | Maximum difference (contralateral eye) (%) |
| 0.01 | −5.6 | −2.8 |
| 0.1 | +9.7 | −2.7 |
| 0.5 | +23.9 | −6.9 |

This Table shows that, contrary to the compounds of the invention, clonidine causes an important mydriasis of the ipsilateral eye, at concentrations (0.1 and 0.5%) which produce no lowering of intraocular pressure.

4. Effects on the mucous membrane of the treated eye (hypohemia).

The effect of the compounds according to the invention on the mucous membrane of the treated eye is demonstrated in awake normotensive rabbits (New Zealand White) of both sexes (2-2.5 kg), by visual examination of the conjunctivae in order to detect possible changes or reactions to the treatment after topical application of the compounds into the eye of the animal. Hypohemia manifests itself by insufficient blood irrigation of the conjunctiva, which can result in irreversible local ischemias. The compounds to be studied are administered as in the previous tests as a solution in 30 microliters of sterile distilled water (collyrium) at concentrations ranging from 0 (reference) to 0.5% (in weight per volume).

At doses effective to lower the intraocular pressure, for example 0.1% for compound A or 0.5% for compound E, the compounds according to the invention do not induce hypohemia. However, with clonidine at a concentration of 0.01%, whitening of the conjunctivae is observed after 30 minutes; this effect is still present after 1 hour for clonidine at a concentration of 0.1%.

5. Effects on the heart rate.

The effect of the compounds on the heart rate is demonstrated in awake normotensive rabbits (New Zealand White) of both sexes (2–2.5 kg), by measuring the heart rate at the level of the caudal artery, after topical application of the compounds into the left eye of the animals. The compounds to be studied are administered as a solution in 30 microliters of sterile distilled water (collyrium) at concentrations ranging from 0 (reference) to 0.5% (in weight per volume).

No significant effect on the heart rate is observed in the animals treated with the compounds according to the invention. However, in animals treated with clonidine at a concentration of 0.01%, the heart rate slows down appreciably by 10.7% after 3 hours, and, in animals treated with clonidine at a concentration of 0.1%, the heart rate slows down significantly by 17.9% after only 1 hour.

6. Toxicity.

The toxicity of the compounds according to the present invention has been determined in male NMRI mice by means of Irwin's test (S. IRWIN, Psychopharmacologia, 13, (1968), 222–257). Progressive doses of the compound to be tested are administered intraperitoneally to groups of three mice until the lethal dose is reached (dose which causes the death of two out of three animals within 24 hours).

Table IV below gives the lethal dose in mg/kg found for the compounds according to the invention. It can be seen from this Table that the compounds of the invention have a very low toxicity.

TABLE IV

| Compound | Toxicity Lethal dose (in mg/kg) |
|---|---|
| A | >216 |
| B | 230 |
| C | 232 |
| D | 25 |
| E | 248 |
| F | 155 |
| G | 416 |

The compounds according to the present invention are preferably administered in the form of an ophthalmic pharmaceutical composition adapted for topical administration to the eye, for example in the form of solutions, ointments or as a solid insert applicable to the eye. The percentage of active product in the pharmaceutical compositions can vary from 0.01 to 1%, preferably from 0.05 to 0.5% by weight. As regards the daily dosage, the compounds according to the present invention are generally administered to the eye in a dose of from 1 µg to 1 mg and preferably of from 50 µg to 0.5 mg of active compound, alone or in admixture.

The ophthalmic pharmaceutical compositions which contain the compounds of the present invention can be conveniently admixed with one or more solid or liquid non-toxic ophthalmologically acceptable carriers. Typical ophthalmologically acceptable carriers are for example water, mixtures of water and water-miscible solvents, such as lower aliphatic or araliphatic alcohols, vegetable oils, polyalkylene glycols, ethyl cellulose, ethyl oleate, carboxymethyl cellulose, polyvinylpyrrolidine, isopropyl myristate and other conventional carriers. The ophthalmic compositions may also contain non-toxic auxiliary substances such as emulsifying, preserving, wetting agents and the like, as for example polyethylene glycols 200, 300, 400, 600, 1,000, 1,500, 4,000, 6,000 and 10,000, bactericides such as quaternary ammonium compounds or phenylmercuric salts, known to have cold sterilizing properties and non-injurious effects, methylparaben, propylparaben, benzyl alcohol, 2-phenylethanol, buffering ingredients such as sodium chloride, sodium borate, sodium acetate or gluconate buffers, and the like.

Additionally, appropriate liquid ophthalmologically acceptable carriers can be used. Examples of these ophthalmic liquid carriers are phosphate-containing buffer solutions, isotonic solutions of boric acid, sodium chloride, sodium borate, and the like.

The ophthalmic compositions may also be in the form of a solid insert for the eye. In this case, one may use a solid water soluble polymer as the carrier for the medicament. The polymer used to form the insert may be any water soluble non-toxic polymer, for example, cellulose derivatives, such as methyl cellulose, sodium carboxymethyl cellulose, hydroxy(lower)alkyl cellulose, such as hydroxyethyl cellulose, hydroxypropyl cellulose, hydroxypropylmethyl cellulose, acrylates, such as polyacrylic acid or polyacrylamides, natural products, such as gelatin, alginates, pectins, tragacanth, starch derivatives, such as starch acetate, hydroxyethyl starch, hydroxypropyl starch, as well as other synthetic derivatives such as polyvinyl alcohol, polyvinylpyrrolidone, polyvinylmethyl ether, polyethylene oxide, and mixtures of said polymers.

If a solid insert is used, it is preferably prepared from cellulose derivatives, such as methyl cellulose, hydroxyethyl cellulose, hydroxypropyl cellulose or from other synthetic materials, such as polyvinyl alcohol, polyvinylpyrrolidone, polyethylene oxide or polyvinylmethyl ether.

As a non-limiting example of a composition containing a compound of the invention, a sterile solution for topical application in the form of a collyrium is given below:

| Ingredients | Quantities (% in w/v) |
|---|---|
| Active compound | 0.01 to about 1% |
| Polyvinyl alcohol | 0 to 40% |
| Benzylalkonium chloride | 0 to 0.15% |
| Sodium chloride | 0 to 10% |
| Buffer | 0.01 to 10% |
| Sterile distilled water | q.s. ad 100% |

The following examples illustrate the invention without limiting it. In these examples, the melting points were determined by differential scanning calorimetry (D.S.C.) using a temperature gradient of 20° C./min. The nuclear magnetic resonance spectra (NMR) were recorded on a 250 MHz Bruker spectrometer in dimethylsulfoxide, using tetramethylsilane as internal standard. The chemical shifts are indicated in δ (ppm). The letters s, d, dd, t, q, b and m indicate a singlet, a doublet, a double doublet, a triplet, a quartet, a broadened peak and a multiplet respectively.

EXAMPLE 1

Preparation of the starting
2-hydroxy-3-[1-(1H-imidazol-4-yl)alkyl]-benzonitriles
of formula II 1. 2-hydroxy-3-(1H-imidazol-4-ylmethyl)-benzonitrile.

This compound is prepared according to the method described in example 3.1 of U.S. Pat. No. 4,923,865.

2. 2-hydroxy-3-[1-(1H-imidazol-4-yl)ethyl]-benzonitrile.

This compound is prepared according to the method described in example 3.2 of U.S. Pat. No. 4,923,865.

EXAMPLE 2

Preparation of substituted
2-hydroxy-3-[1-(1H-imidazol-4-yl)alkyl]-benzenecarboximidamides of formula I 1. 2-hydroxy-3-(1H-imidazol-4-ylmethyl)-benzenecarboximidamide.

a) A suspension of 10 g (0.050 mole) of 2-hydroxy-3-(1H-imidazol-4-ylmethyl)-benzonitrile (prepared in example 1.1 above) in 200 ml of methanol is cooled to $-40°$ C. and saturated with gaseous hydrochloric acid. The mixture is then slowly allowed to return to between 0° and 5° C. and the reaction mixture is kept at that temperature for 20 hours. The solution is concentrated to 9/10 of its volume, 300 ml of ice-cold water is added to the residue, and the resulting solution is neutralized with an aqueous sodium bicarbonate solution. The solution is extracted 4 times with 150 ml of ethyl acetate and the organic phases are combined. The organic phase is washed with 100 ml of a saturated aqueous sodium chloride solution, then dried over magnesium sulfate, filtered and evaporated under reduced pressure.

b) The residue thus obtained is taken up in 150 ml of absolute ethanol. The solution is cooled below 10° C. and is saturated with ammonia. The solution is allowed to return to ambient temperature and the reaction mixture is kept at that temperature for 15 hours. The solvent is evaporated under reduced pressure. The residue is purified by preparative liquid chromatography (silica: 600 g; eluent: 77.5:20:2.5 (v/v/v) mixture of dichloromethane-methanol-ammonia). 8 g of a white solid product are isolated and recrystallized from methanol. 4.55 g of 2-hydroxy-3-(1H-imidazol-4-ylmethyl)-benzenecarboximidamide are obtained. Yield: 42%.

M.P.: 248.71° C. NMR: δ: 3.68 (2H,s), 6.13 (1H,dd), 6.61 (1H,s), 6.95 (1H,dd), 7.41 (1H,d), 7.43 (1H,dd). Analysis for $C_{11}H_{12}N_4O$ in %: calculated: C 61.10 H 5.59 N 25.91 found: 61.18 5.62 26.07

2. 2-hydroxy-3-(1H-imidazol-4-ylmethyl)-N-methyl-benzenecarboximidamide.

a) A suspension of 19.9 g (0.1 mole) of 2-hydroxy-3-(1H-imidazol-4-ylmethyl)-benzonitrile (prepared in example 1.1 above) in 600 ml of methanol, cooled to 10° C., is saturated with gaseous hydrochloric acid. 60 ml of water are added, the suspension is cooled to $-25°$ C. and is saturated once again with gaseous hydrochloric acid. The reaction mixture is kept at that temperature for 15 hours. The solution is evaporated and the residue is taken up in 500 ml of ice-cold water; the resulting suspension is neutralized with an aqueous sodium bicarbonate solution. The solution is extracted 4 times with 250 ml of ethyl acetate and the organic phases are combined. The organic phase is washed with 200 ml of a saturated aqueous sodium chloride solution, is then dried over magnesium sulfate, filtered and evaporated. 19.1 g of methyl 2-hydroxy-3-(1H-imidazol-4-ylmethyl)benzenecarboximidate are obtained which are used as such in the following step.

b) 9.55 g (0.0413 mole) of methyl 2-hydroxy-3-(1H-imidazol-4-ylmethyl)-benzenecarboximidate are dissolved in 100 ml of absolute ethanol, the solution is cooled to 10° C. and 1.28 g (0.0413 mole) of methylamine are added thereto. The solution is allowed to return to ambient temperature and is allowed to react for 15 hours. The solvent is evaporated under reduced pressure. The residue is purified by preparative liquid chromatography (silica: 600 g; eluent: 78:20:2 (v/v/v) mixture of ethyl acetate-methanol-ammonia). 9.49 g of product are isolated and stirred in 100 ml acetonitrile at 50° C. for 30 minutes. The solid product is filtered off and recrystallized from methanol. 4.5 g of 2-hydroxy-3-[1-(1H-imidazol-4-ylmethyl)-N-methyl-benzenecarboximidamide are obtained. Yield: 47%.

M.P.: 235.84° C. NMR: δ: 2.94 (3H,s), 3.70 (2H,s), 6.20 (1H,dd), 6.60 (1H,s), 6.95 (1H,dd), 7.41 (1H,d), 7.47 (1H,dd), 8.47 (2H,m), 14.1 (1H,m). Analysis for $C_{12}H_{14}N_4O$ in %: calculated: C 62.59 H 6.15 N 24.73 found: 62.53 6.15 24.30

3. 2-(4,5-dihydro-1H-imidazol-2-yl)-6-(1H-imidazol-4-ylmethyl)-phenol.

a) Methyl 2-hydroxy-3-(1H-imidazol-4-ylmethyl)-benzenecarboximidate is prepared as in 2.a) above and is used as such in the following step.

b) 9.55 g (0.0413 mole) of the product prepared in 3.a) above are dissolved in 100 ml of absolute ethanol and 6.65 ml (0.0826 mole) of ethylenediamine are added thereto. This solution is stirred for one hour at ambient temperature and then allowed to react for 15 hours. The precipitate which has formed is filtered off (1st crop). The filtrate is evaporated under reduced pressure and the residue thus obtained is purified by preparative liquid chromatography (silica: 400 g; eluent; 78:20:2 (v/v/v) mixture of methyl acetate-methanol-ammonia). 1.7 g of a white solid compound is isolated (2nd crop). The two crops are combined and recrystallized twice from methanol. 3.3 g of 2-(4,5-dihydro-1H-imidazol-2-yl)-6-(1H-imidazol-4-ylmethyl)-phenol are obtained. Yield: 33%.

M.P.: 260.92° C. NMR: δ: 3.71 (3H,S), 3.77 (2H,s), 6.53 (1H,t), 6.64 (1H,s), 7.07 (1H,d), 7.40 (1H,dd), 7.45 (1H,s), 11.1 (2H,m), 11.7 (1H,m). Analysis for $C_{13}H_{14}N_4O$ in %: calculated: C 64.46 H 5.82 N 23.13 found: 64.46 5.86 23.14

4. 2-hydroxy-3-[1-(1H-imidazol-4-yl)ethyl]-benzenecarboximidamide.

a) A suspension of 10 g (0.047 mole) of 2-hydroxy-3-[1-(1H-imidazol-4-yl)ethyl]-benzonitrile (prepared in example 1.2 above) in 100 ml of methanol is cooled to $-40°$ C. and saturated with gaseous hydrochloric acid. The mixture is allowed to return to 5° C. and is kept at that temperature for 24 hours. The solution is concentrated in the cold to ¾ of its volume; 200 ml of water and 150 ml of ethyl acetate are added to the residue, and the resulting mixture is neutralized with an aqueous sodium bicarbonate solution. The solution is extracted 3 times with 100 ml of ethyl acetate and the organic phases are combined. The organic phase is washed with 100 ml of a saturated aqueous sodium chloride solution, then dried over magnesium sulfate, filtered and the solvent is evaporated under reduced pressure at ambient temperature.

b) The residue thus obtained is taken up in 50 ml of absolute ethanol, the solution is cooled below 10° C. and is saturated with gaseous ammonia. The solution is then allowed to return to ambient temperature and the reaction mixture is kept at that temperature for 6 hours. The solvent is then evaporated under reduced pressure. The resulting residue is purified by preparative liquid chromatography (silica: 500 g; eluent: 78:20:2 (v/v/v) mixture of dichloromethane-methanol-ammonia). The product obtained after evaporation of the solvents is recrystallized twice from a 90/10 (v/v) mixture of water-methanol. 8.75 g of 2-hydroxy-3-[1-(1H-imidazol-4-yl)ethyl]-benzenecarboximidamide are obtained. Yield: 81%.

M.P.: 190.6° C. NMR: δ: 1.40 (3H,s), 4.48 (1H,q), 6.14 (1H,dd), 6.63 (1H,s), 6.88 (1H,dd), 7.40 (1H,s) 7.41 (1H,dd). Analysis for $C_{12}H_{14}N_4O$ in %: calculated: C 62.59 H 6.13 N 24.33 found: 62.58 6.12 24.37

5. N,2-dihydroxy-3-(1H-imidazol-4-ylmethyl)-benzenecarboximidamide.

a) A suspension of 14.1 g (0.071 mole) of 2-hydroxy-3-(1H-imidazol-4-ylmethyl)-benzonitrile (prepared in example 1.1 above) in 420 ml of methanol is cooled to −40° C. and saturated with gaseous hydrochloric acid. The suspension is allowed to return to 10° C. and is saturated once again with gaseous hydrochloric acid. The reaction mixture is kept at that temperature for 20 hours. The solution is concentrated to 200 ml, 300 ml of ice-cold water and 300 ml of ethyl acetate are added to the concentrated solution and the solution is then neutralized using an aqueous sodium bicarbonate solution. The solution is filtered, and the aqueous phase is separated from the organic phase, then the aqueous phase is extracted twice with 300 ml of ethyl acetate and the organic phases are combined. The organic phase is washed with a saturated aqueous sodium chloride solution, is then dried over magnesium sulfate, filtered and evaporated under reduced pressure. 15.4 g of methyl 2-hydroxy-3-(1H-imidazol-4-ylmethyl)-benzenecarboximidate are obtained as a beige solid product which is taken up in 210 ml of absolute ethanol.

b) 1.53 g (0.022 mole) of hydroxylamine hydrochloride and 3.06 ml (0.22 mole) of triethylamine are added to 70 ml of the methyl 2-hydroxy-3-(1H-imidazol-4-ylmethyl)-benzenecarboximidate solution in absolute methanol prepared in 5.a) above. The mixture is allowed to react for one hour at 20° C. The solvent is evaporated under reduced pressure, and the oily residue is taken up by the application of ultrasound in 100 ml of water. 4.5 g of a white solid product are isolated which are recrystallized twice from methanol. 3.4 g of N,2-dihdroxy-3-(1H-imidazol-4-ylmethyl)benzenecarboximidamide are obtained. Yield: 62%.

M.P.: 227.81° C. NMR: δ: 3.83 (2H,s), 6.24 (2H,s), 6.67 (1H,s), 6.75 (1H,t), 7.05 (1H,d), 7.49 (1H,s), 7.51 (1H,d), 10.07 (1H,m), 11.7 (1H,m), 12.5 (1H,m). Analysis for $C_{11}H_{12}N_4O_2$ in %: calculated: C 56.88 H 5.21 N 24.13 found: 56.83 5.25 24.09

6. 2-hydroxy-3-(1H-imidazol-4-ylmethyl)-benzenecarboximidic acid hydrazide.

a) A suspension of 14.1 g (0.071 mole) of 2-hydroxy-3-(1H-imidazol-4-ylmethyl)-benzonitrile (prepared in example 1.1 above) in 400 ml of methanol is cooled to −45° C. and saturated with gaseous hydrochloric acid. The suspension is allowed to return to 10° C. and gaseous hydrochloric acid is bubbled through the suspension for 4 hours more at that temperature. The suspension is cooled to 5° C. and kept at that temperature for 20 hours. The precipitate which has formed is filtered off and 11.4 g of methyl 2-hydroxy-3-(1H-imidazol-4-ylmethyl)-benzenecarboximidate are obtained in the form of a white solid which is used as such in the following step.

b) A solution of 2 g (0.0066 mole) of methyl 2-hydroxy-3-(1H-imidazol-4-ylmethyl)-benzenecarboximidate prepared in 6.a) above in 20 ml of methanol is added in one go to a solution of 1.52 ml (0.0033 mole) of hydrazine hydrate in 20 ml of methanol. The reaction is allowed to proceed for 15 minutes, then 40 ml of diethyl ether are added. The precipitate which has formed is filtered off and the filtrate is concentrated under reduced pressure. The evaporation residue is purified by preparative liquid chromatography (silica: 400 g; eluent: 89:10:1 (v/v/v) mixture of dichloromethane-methanol-ammonia). The pale yellow solid product obtained after evaporation of the solvents is recrystallized from methanol. 1.2 g of 2-hydroxy-3-(1H-imidazol-4-ylmethyl)-benzenecarboximidic acid hydrazide are obtained. Yield: 80%.

M.P.: 187.8° C. NMR: δ: 3.77 (2H,s), 5.09 (2H,b), 6.34 (2H,b), 6.56 to 6.64 (2H,m), 6.97 (1H,d), 7.44 (2H,m), 11.7 (1H,b), 14.7 (1H,b). Analysis for $C_{11}H_{13}N_5O.\frac{1}{2}H_2O$ in %: calculated: C 54.98 H 5.87 N 29.15 found: 54.96 5.89 28.39

EXAMPLE 3

Preparation of N,2-dihydroxy-3-(1H-imidazol-4-ylmethyl)-benzenecarboximidamide 3 g (0.015 mole) of 2-hydroxy-3-(1H-imidazol-4-ylmethyl-)benzonitrile (prepared in example 1.1 above) are dissolved in 100 ml of methanol and 1.15 g (0.0165 mole) of hydroxylamine hydrochloride and 1.84 g of sodium acetate are added thereto. The resulting mixture is then heated at the reflux temperature for 20 hours. The methanol is evaporated under reduced pressure and the residue is taken up in 100 ml of water. The resulting aqueous solution is neutralized to pH 7 by addition of an aqueous sodium bicarbonate solution. The white precipitate thus formed is filtered off, dried under vacuum and recrystallized from methanol. 1.6 g of N,2-dihydroxy-3-(1H-imidazol-4-ylmethyl)-benzenecarboximidamide, identical to the product obtained in example 2.5 above, are obtained. Yield 46%.

EXAMPLE 4

Preparation of optically active 2-hydroxy-3-[1-(1H-imidazol-4-yl)ethyl]-benzenecarboximidamides.
(−)-2-hydroxy-3-[1-(1H-imidazol-4-yl)ethyl]-benzenecarboximidamide and
(+)-2-hydroxy-3-[1-(1H-imidazol-4-yl)ethyl]-benzenecarboximidamide .

a) Methyl 2-hydroxy-3-[1-(1H-imidazol-4-yl)ethyl]-benzenecarboximidate is prepared as in example 2.2.a), starting from 32 g (0.150 mole) of 2-hydroxy-3-[1-(1H-imidazol-4-yl)ethyl]-benzonitrile (prepared in example 1.2). The crude residue of methyl 2-hydroxy-3-[1-(1H-imidazol-4-yl)ethyl]-benzenecarboximidate is used as such in the following step.

b) The residue obtained in a) above is taken up in 150 ml of absolute ethanol, and 38.7 ml (0.3 mole) of S-(−)-α-methylbenzylamine are added thereto. The resulting mixture is allowed to react at ambient temperature for 15 hours, then the solvent is evaporated under reduced pressure. The residue thus obtained is purified by preparative liquid chromatography (silica: 1 kg; eluent:

95.6:4:0.4 (v/v/v) mixture of chloroform-methanol-ammonia).

c) The partially purified mixture of diastereoisomers is then chromatographed in 5 g fractions (silica: 1 kg; eluent: 94.5:5:0.5 (v/v/v) mixture of ethyl acetate-methanol-ammonia) in order to achieve complete separation of the diastereoisomers. The two diastereoisomers which are then substantially pure are chromatographed one last time under the same conditions. 18.9 g (yield: 33%) of diastereoisomer A, the less polar isomer which is eluted first, and 27.3 g of diastereoisomer B (yield 47%), the more polar isomer which is eluted last, are obtained. These two compounds are used respectively in the final debenzylation step.

NMR of diastereoisomer A: δ: 1.40 (3H,d), 1.51 (3H,d), 4.53 (1H,q), 4.99 (1H,q), 6.29 (1H, dd), 6.65 (1H,s), 6.91 (1H,dd), 7.2 to 7.5 (7H,m), 7.75 (1H,m).

NMR of diastereoisomer B: δ: 1.40 (3H,d), 1.52 (3H,d), 4.53 (1H,q), 4.99 (1H,q), 6.27 (1H, dd), 6.67 (1H,s), 6.89 (1H,dd), 7.2 to 7.5 (7H,m), 7.75 (1H,m).

d) (−)-2-hydroxy-3-[1-(1H-imidazol-4-yl)ethyl]-benzenecarboximidamide.

A solution containing 30 g of diastereoisomer A (isolated in c) above) is heated under reflux for 24 hours in 300 ml of a 12N aqueous hydrochloric acid solution and 30 ml of toluene. After removal of a residual solid by filtration, the organic phase is decanted off and the aqueous phase is washed with a little toluene. The aqueous phase is then made alkaline (pH 9) using a 1N aqueous sodium hydroxide solution. This aqueous solution is then extracted with an 80:20 (v/v) mixture of ethyl acetate-methanol. Evaporation of the organic solvents used for extraction yields a solid residue (first crop). The aqueous phase is also evaporated and the residue thus obtained is taken up in 30 ml of a 2.5N ammonia solution in isopropyl alcohol. The insoluble salts are filtered off and the isopropyl alcohol is evaporated to give a solid residue (2nd crop). The two crops are combined and purified by two successive preparative liquid chromatography procedures performed under the same conditions (silica: 1 kg; eluent: 78:20:2 (v/v/v) mixture of dichloromethane-methanol-ammonia). 10 g of a white solid product are isolated and recrystallized from water. 7.18 g of (−)-2-hydroxy-3-[1-(1H-imidazol-4-yl)ethyl]-benzenecarboximidamide monohydrate are obtained. Yield: 32%.

M.P.: 125.18° C. NMR: δ: 1.40 (3H,d), 4.44 (1H,q), 6.16 (1H, t), 6.65 (1H,s), 6.90 (1H,dd), 7.41 (1H,dd), 7.44 (1H,s). $[\alpha]_D^{25} = -232.36°$ (c=1, methanol) Analysis for $C_{12}H_{14}N_4O.H_2O$ in %: calculated: C 58.04 H 6.49 N 22.57 found: 57.86 6.54 22.65 e) (+)-2-hydroxy-3-[1-(1H-imidazol-4-yl)ethyl]-benzenecarboximidamide.

A solution containing 27.3 g of diastereoisomer B (isolated in c) above) is heated under reflux for 24 hours in 270 ml of a 12N aqueous hydrochloric acid solution and 27 ml of toluene. The organic phase is decanted off and the aqueous phase washed with a little toluene. The aqueous phase is evaporated under reduced pressure and the residue is taken up in 100 ml of ethanol. The ethanolic solution is then neutralized with 40 ml of a 2.5N ammonia solution in isopropyl alcohol. The insoluble salts are then filtered off and the filtrate is evaporated. The residue thus obtained is purified by two successive preparative liquid chromatography procedures performed under the same conditions (silica: 800 g; eluent: 78:20:2 (v/v/v) mixture of dichloromethane-methanol-ammonia). 6.22 g of a white solid product are isolated, which are recrystallized from water. 4.93 g of (+)-2-hydroxy-3-[1-(1H-imidazol-4-yl)ethyl]-benzenecarboximidamide monohydrate are obtained. Yield: 24%.

M.P.: 139.07° C. NMR: δ: 1.40 (3H,d), 4.48 (1H,q), 6.14 (1H, t), 6.63 (1H,s), 7.40 (1H,s), 7.41 (1H,dd). $[\alpha]_D^{25} = +237.44°$ (c=1, methanol) Analysis for $C_{12}H_{14}N_4O.H_2O$ in %: calculated: C 58.04 H 6.49 N 22.57 found: 58.11 6.53 22.65

EXAMPLE 5

Preparation of substituted 2-hydroxy-3-[1-(1H-imidazol-4-yl)alkyl]-benzenecarboximidamides of formula I 1. 2-hydroxy-3-(1H-imidazol-4-ylmethyl)-benzenecarboximidamide.

a) 11.3 ml (0.0088 mole) of S-(−)-α-methylbenzylamine are added to 140 ml of the solution of methyl 2-hydroxy-3-(1H-imidazol-4-ylmethyl]-benzenecarboximidate in absolute ethanol prepared in example 2.5.a) above. The reaction is allowed to proceed for 15 hours at 20° C., then the solvent is evaporated under reduced pressure. The residue thus obtained is purified by preparative liquid chromatography (silica: 1 kg; eluent: 94.5:5:0.5 (v/v/v) mixture of ethyl acetate-methanol-ammonia). 13.9 g of 2-hydroxy-3-(1H-imidazol-4-ylmethyl)-N-α-methylbenzyl-benzenecarboximidamide are thus obtained which are used as such in the following step.

b) For analysis purposes, 2 g of 2-hydroxy-3-(1H-imidazol-4-ylmethyl )-N-α-methylbenzyl-benzenecarboximidamide prepared in 1.a) above are chromatographed once more (silica: 500 g; eluent: 92.3:7:0.7 (v/v/v) mixture of dichloromethane-methanol-ammonia).

NMR: δ: 1.52 (3H,d), 3.74 (2H,m), 5.00 (1H,q), 6.28 (1H,t), 6.64 (1H,s), 6.96 (1H,dd), 7.25 to 7.45 (6H,m), 7.51 (1H,dd), 7.80 (1H,b). $[\alpha]_D^{25} = +225°$ (c=1, methanol).

c) 1 g (0.0031 mole) of 2-hydroxy-3-(1H-imidazol-4-ylmethyl)-N-α-methylbenzyl-benzenecarboximidamide prepared in 1.a) above and 15 ml of ammonia are placed in a digester and heated at 100° C. for 40 hours. The solvent is evaporated and the residue is purified by preparative liquid chromatography (silica: 200 g; eluent: 78:20:2 (v/v/v) mixture of dichloromethane-methanol-ammonia). After evaporation of the solvents, 0.5 g of 2-hydroxy-3-(1H-imidazol-4-ylmethyl)-benzenecarboximidamide, identical to the compound prepared in example 2.1, is obtained. Yield: 75%.

2. 2-hydroxy-3-(1H-imidazol-4-ylmethyl)-N-(1-methylethyl)-benzenecarboximidamide.

5 g (0.0156 mole) of 2-hydroxy-3-(1H-imidazol-4-ylmethyl)-N-α-methylbenzyl-benzenecarboximidamide prepared in 1.a) above and 50 ml of 2-propanamine are placed in a digester and are heated at 80° C. for 54 hours, then at 100° C. for 46 hours. The solvent is evaporated and the residue is purified by preparative liquid chromatography (silica: 600 g; eluent: 89:10:1 (v/v/v) mixture of dichloromethane-methanol-ammonia). After evaporation of the solvents, 3.6 g of a pale yellow solid product are obtained which are recrystallized twice from acetonitrile. 1.25 g of 2-hydroxy-3-(1H-imidazol-4-ylmethyl)-N-(1-methylethyl)-benzenecarboximidamide are obtained. Yield: 31%.

M.P.: 138–139° C. (decomposition). NMR: δ: 1.24 (6H,d), 3.70 (2H,s), 3.91 (1H,m), 6.20 (1H,t), 6.60 (1H,s), 6.94 (1H,d), 7.43 (1H,s), 7.48 (1H,dd), 7.98 (1H,b), 11.7 (1H,b). Analysis for $C_{14}H_{18}N_4O \cdot H_2O$ in %: calculated: C 60.85 H 7.30 N 20.28 found: 60.62 7.67 19.88

We claim:

1. A substituted 2-hydroxy-3-[1-(1H-imidazol-4-yl)alkyl]-benzenecarboximidamide, its optically active isomers or racemic mixtures, of the formula

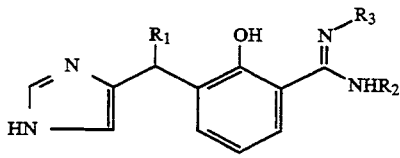

wherein $R_1$ represents a hydrogen atom or an alkyl radical having 1 to 4 carbon atoms, $R_2$ represents a hydrogen atom, a hydroxyl group, an amino group or an alkyl radical having 1 to 4 carbon atoms, $R_3$ represents a hydrogen atom, or $R_2$ and $R_3$ taken together represent a $-CH_2-CH_2-$ group; or a non-toxic ophthalmologically acceptable acid addition salt thereof.

2. A compound as claimed in claim 1, namely 2-hydroxy-3-(1H-imidazol-4-ylmethyl)-benzenecarboximidamide or a non-toxic, ophthalmologically acceptable acid addition salt thereof.

3. A compound as claimed in claim 1, namely N,2-dihydroxy-3-(1H-imidazol-4-ylmethyl)-benzenecarboximidamide or a non-toxic, ophthalmologically acceptable acid addition salt thereof.

4. A compound as claimed in claim 1, namely 2-hydroxy-3-(1H-imidazol-4-ylmethyl)-N-methyl-benzenecarboximidamide or a non-toxic, ophthalmologically acceptable acid addition salt thereof.

5. A compound as claimed in claim 1, namely 2-hydroxy-3-[1-(1H-imidazol-4-yl)ethyl]-benzenecarboximidamide or a non-toxic, ophthalmologically acceptable acid addition salt thereof.

6. A compound as claimed in claim 1, namely (+)-2-hydroxy-3-[1-(1H-imidazol-4-yl)ethyl]-benzenecarboximidamide or a non-toxic, ophthalmologically acceptable acid addition salt thereof.

7. A compound as claimed in claim 1, namely (−)-2-hydroxy-3-[1-(1H-imidazol-4-yl)ethyl]-benzenecarboximidamide or a non-toxic, ophthalmologically acceptable acid addition salt thereof.

8. A compound as claimed in claim 1, namely 2-(4,5-dihydro-1H-imidazol-2-yl)-6-(1H-imidazol-4-ylmethyl)-phenol or a non-toxic, ophthalmologically acceptable acid addition salt thereof.

9. A compound as claimed in claim 1, namely 2-hydroxy-3-(1H-imidazol-4-ylmethyl)-N-(1-methylethyl)-benzenecarboximidamide or a non-toxic, ophthalmologically acceptable acid addition salt thereof.

10. A compound as claimed in claim 1, namely 2-hydroxy-3-(1H-imidazol-4-ylmethyl)-benzenecarboximidic acid hydrazide or a non-toxic, ophthalmologically acceptable acid addition salt thereof.

11. An ophthalmic composition for the lowering of the intraocular pressure comprising an effective amount of a substituted 2-hydroxy-3-[1-(1H-imidazol-4-yl)alkyl]-benzenecarboximidamide as claimed in claim 1, and one or more solid or liquid non-toxic ophthalmologically acceptable carriers therefor.

12. A method for the prevention and the treatment of glaucoma and of lowering intraocular pressure in a patient in need thereof, which comprises topically applying to the eye of said patient an effective amount of a substituted 2-hydroxy-3-[1-(1H-imidazol-4-yl)alkyl]-benzenecarboximidamide as claimed in claim 1.

* * * * *

UNITED STATES PATENT AND TRADEMARK OFFICE
CERTIFICATE OF CORRECTION

PATENT NO. : 5,385,927
DATED : January 31, 1995
INVENTOR(S) : PHILIPPE MICHEL, ERIC COSSEMENT, JEAN GOBERT and ERNST WULFERT It is certified that error appears in the above-indentified patent and that said Letters Patent is hereby corrected as shown below:

On the cover page, Item [30]

"[DE] Germany" should be deleted and replaced by "[GB] Great Britain".

Column 1, line 8, correct the spelling of "ophthalmologically".

Column 5, line 32, change "[1(1H-imidazol-4-yl)alkyl]" to read "[1-(1H-imidazol-4-yl)alkyl]".

Signed and Sealed this

Twenty-seventh Day of June, 1995

Attest:

BRUCE LEHMAN

Attesting Officer    Commissioner of Patents and Trademarks